United States Patent [19]
Clinton

[11] Patent Number: 5,872,314
[45] Date of Patent: Feb. 16, 1999

[54] METHOD AND APPARATUS FOR MEASURING CHARACTERISTICS OF MEAT

[76] Inventor: Robert P. Clinton, 701 Carlisle Dr., Arnold, Md. 21012

[21] Appl. No.: 900,356

[22] Filed: Jul. 25, 1997

[51] Int. Cl.$^6$ .............................. A61B 8/00; G01N 29/08
[52] U.S. Cl. .......................... 73/602; 600/449; 600/443; 73/620
[58] Field of Search .............................. 73/597, 598, 599, 73/600, 602, 606, 628, 629, 620; 600/442, 443, 444, 445, 446, 447, 448, 449, 437; 382/110

[56] References Cited

U.S. PATENT DOCUMENTS

| | | | |
|---|---|---|---|
| 4,138,999 | 2/1979 | Eckhart et al. | 600/449 |
| 4,359,055 | 11/1982 | Carlson | 600/449 |
| 4,785,817 | 11/1988 | Stouffer | 600/443 |
| 5,208,747 | 5/1993 | Wilson et al. | 600/443 |
| 5,339,815 | 8/1994 | Liu et al. | 600/437 |
| 5,353,796 | 10/1994 | Schroeder et al. | 600/437 |
| 5,398,290 | 3/1995 | Bretbour | 382/128 |
| 5,520,183 | 5/1996 | Lake et al. | 600/453 |
| 5,573,002 | 11/1996 | Pratt | 600/443 |
| 5,613,493 | 3/1997 | Schafer | 600/442 |
| 5,617,864 | 4/1997 | Stouffer et al. | 600/459 |
| 5,625,147 | 4/1997 | Miles et al. | 73/597 |
| 5,641,907 | 6/1997 | Haagensen | 73/620 |
| 5,673,647 | 10/1997 | Pratt | 119/51.02 |
| 5,685,307 | 11/1997 | Holland et al. | 600/437 |
| 5,717,142 | 2/1998 | Schafer | 73/597 |

OTHER PUBLICATIONS

Bosoon Park et al., *Determination of Beef Marbling Score Using Ultrasound A–Scan*, ASAE Technical Paper 90–6058 written for presentation at the 1990 International Summer Meeting of the American Society of Agricultural Engineers, Jun. 24–27, 1990.

Bosoon Park et al., *Ultrasonic Frequency Analysis for Beef Quality Grading*, Paper No. 906573 written for presentation at the 1990 International Winter Meeting of the American Society of Agricultural Engineers, Dec. 18–21, 1990.

Keith A. Wear et al., *Application of Autoregressive Spectral Analysis to Cepstral Estimation of Mean Scatterer Spacing*, IEEE Transactions on Ultrasonics, Ferroeletrics, and Frequency Control, vol. 40, No. 1, Jan. 1993.

*Primary Examiner*—Hezron Williams
*Assistant Examiner*—Rose M. Miller
*Attorney, Agent, or Firm*—Dickstein Shapiro Morin & Oshinsky LLP

[57] ABSTRACT

A method and apparatus for measuring characteristics of meat, such as beef. More particularly, the invention uses quantitative analysis of ultrasonic A scan signals to measure the following characteristics of meat in real time: the percentage of intramuscular fat, the quality grade, the merit number, the depth of back fat and the approximate size of a predetermined rib eye area. The ultrasonic A scan signals are measured above the twelfth rib, above the thirteenth rib and between the twelfth and thirteenth ribs. The invention can be used with either live or processed animals.

44 Claims, 11 Drawing Sheets

FIG. 8 Individual Grade Spectrum

FIG. 9 Mean Grade Spectrum

METHOD AND APPARATUS FOR MEASURING CHARACTERISTICS OF MEAT

FIELD OF THE INVENTION

The invention relates to a method and apparatus for measuring characteristics of meat, such as beef. More particularly, the invention uses quantitative analysis of an ultrasonic A scan signal to measure the following characteristics of meat: the percentage of intramuscular fat, the quality grade, the merit number, the depth of back fat and the approximate size of a predetermined rib eye area. Ultrasonic A scan signals are measured above the twelfth rib, above the thirteenth rib and between the twelfth and thirteenth ribs. The invention can be used with either live or slaughtered animals.

BACKGROUND OF RELATED ART

Traditionally, meat is visually inspected and graded after an animal has been slaughtered. With beef, for example, a cut is made between the 12th and 13th rib. A grader then visually inspects the exposed meat. Based on the appearance of this cross section, the grader classifies the meat according to predetermined standards that reflect the amount of fat, or marbling, present in the meat. Typically, beef is classified according to U.S. Department of Agriculture (USDA) guidelines. Under USDA guidelines, meat can be classified as standard, select, choice or prime.

The visual inspection of meat has several disadvantages. First, the grading is subjectively based on the opinion of the grader. Different graders may assign different grades to the same piece of meat. Even the same grader might assign different grades to the same meat on different days. This is extremely important because the value of the meat is directly dependent on the grade it is assigned.

Visual grading of meat is also limited because the grader only has access to an area of the meat exposed at the cut. Generally, this grading is based solely on the quality of the meat at the cut between the 12th and 13th ribs. If that area does not accurately reflect the entire side of meat, the grade assigned to the meat will be incorrect.

Moreover, traditional techniques only provide information based on what is visually apparent to the grader. While the grader can visually estimate the marbling of the beef there is no way for him to determine the flavor and tenderness, or "merit," of the meat. This is important because one out of four sides of beef classified as "prime" is still rejected as unsatisfactory by discriminating customers, such as restaurants specializing in beef steak.

The traditional method obviously cannot be used to grade the quality of live cattle. Knowing exactly when to slaughter cattle is important to maximize profits. Ranchers send herds of cattle to feed lots prior to processing. The feed lots attempt to create the highest quality meat at the lowest cost. Currently, feed lots must estimate when an entire group, or pen, of cattle has been sufficiently fed. A pen might contain 50, 100, or even 150 head of cattle. If the cattle have not been fed long enough the quality of the meat, and its value, suffers. On the other hand, if the cattle are fed too long the increase in the quality of the meat will not justify the extra expense of feeding the animals plus a reduced grade penalty. Because there is no way to determine the quality of live cattle, an owner can only estimate the point of maximum profitability for a particular animal. For example, feed lot operators generally hold all pens a fixed number of days selected to maximize profits. Even with this approach, however, about one third of the individual animals in any given pen are under-fed and one third are over-fed. It would be desirable to know the quality of each animal in the pen so every animal can be processed at the peak of its profitability.

Because the traditional technique can only be used on slaughtered animals, it is of limited use when attempting to breed a more profitable herd. If the cattle owner had instant feedback about the quality of the animals in the herd, higher quality animals could be selected for breeding. This would improve the genetic quality of the herd over time. Currently, the cattle owner must wait until an animal has left the feed lot and been slaughtered before any decisions about the genetic quality of the animal can be made.

The lack of instant feedback also prevents a cattle owner from responding to changes in consumer preferences. If consumers begin to demand leaner meat, for example, the cattle owner cannot make decisions about a herd until each animal has left the feed lot and has been slaughtered. This process can take up to six months or more.

To overcome some of these limitations, ultrasound technology has been used for the last two decades in animal research and applications. Ultrasound scanning technology utilizes high frequency sound waves to collect information from live tissue in a non-invasive manner. Efforts in the ultrasonic measurement of meat have concentrated on the use of real-time "B" mode imaging. B mode ultrasound, often used in medical applications, provides the operator with a two dimensional picture of the tissue being inspected. Brightness and texture are used in the image to characterize the animal's muscle tissue. By studying the two-dimensional image, the operator can characterize the muscle tissue and grade the animal. This approach, however, suffers from the same limitation as the traditional method because it is still based on the subjective opinion of the operator. Additionally, operators must be highly trained to interpret the B mode images correctly.

There have been attempts to mechanize and computerize the use of B mode imaging. Obtaining accurate measurements of these tissue characteristics is difficult because of speckle noise present in the image. Moreover, B mode imaging equipment is extremely expensive and transducers used with B mode imaging quickly wear out when used on rough surfaces, such as the hide of an animal Equipment used with B mode imaging is also very large and does not lend itself to use in the field. Finally, B mode imaging is not able to determine the flavor and tenderness, or "merit," of the meat.

SUMMARY OF THE INVENTION

It is thus apparent from the above that there exists a significant need in the art for an improved method and apparatus for measuring characteristics of meat. Specifically, a more promising approach is disclosed to extract and identify features using the acoustic parameters of a back scattered ultrasound A scan signal. A quantitative analysis of the A scan signal provides definitive information about the characteristics of the meat.

It is therefore an object of this invention to provide a method and apparatus for measuring characteristics of meat using ultrasonic A scan signals.

It is another object of this invention to provide a method and apparatus for measuring the percentage of fat, the quality grade, the merit, the depth of back fat and the size of predetermined areas of meat.

It is another object of this invention to provide an inexpensive, real-time, durable and objective method and apparatus for measuring characteristics of meat.

It is another object of this invention to provide a method and apparatus for measuring characteristics of meat in both live and slaughtered animals.

Briefly described, these and other objects of the invention are accomplished by providing a method of measuring characteristics of meat. An ultrasonic A scan transducer is positioned on the animal to be measured and an A scan signal is transmitted into the meat. The return signal is measured and used to calculate characteristics of the meat. Return signals are measured above the twelfth rib, above the thirteenth rib and between the twelfth and thirteenth ribs.

The present invention also provides an apparatus for measuring characteristics of meat, including an A scan transducer that transmits an ultrasonic signal into the meat and receives a return signal. The transducer is connected to a computer that calculates characteristics of the meat based on the return signal. A second computer can be connected through a communication network and used to analyze the return signals collected by the computer with the transducer With these and other objects, advantages and features of the invention that may become apparent, the nature of the invention may be more readily understood by reference to the following detailed description of the invention, the appended claims and to the several drawings attached herein.

DETAILED DESCRIPTION OF PREFERRED EMBODIMENTS

Figure 1:
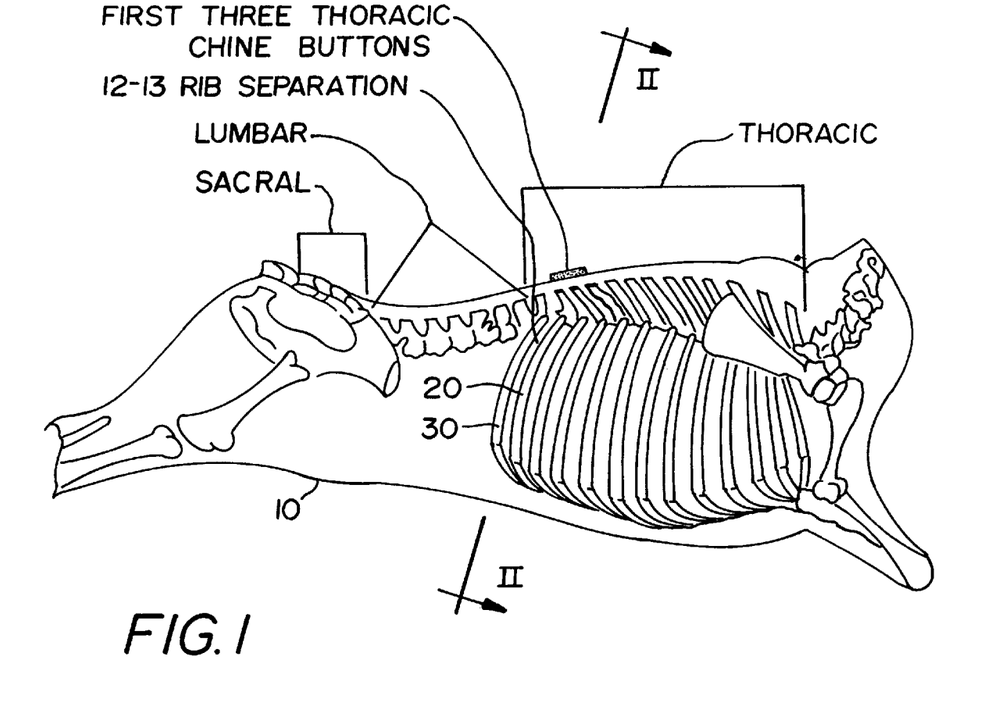
FIG. 1 shows a side skeletal view of a steer.

Referring now in detail to the drawings wherein like parts are designated by like reference numerals throughout, there is illustrated in FIG. 1 a side skeletal view of a beef animal 10. A grader generally has a cut between the twelfth rib 20 and the thirteenth rib 30 to grade the quality of the meat in the beef animal 10. In the preferred embodiment of the present invention, ultrasonic A scan transducer signals are measured at the following three locations: (1) above the twelfth rib 20; (2) above the thirteenth rib 30; and (3) between the twelfth rib 20 and the thirteenth rib 30. The phrase "above the rib" implies that the transducer is placed on the hide of the animal at the point closest to the rib at an angle as described below.

Figure 2:
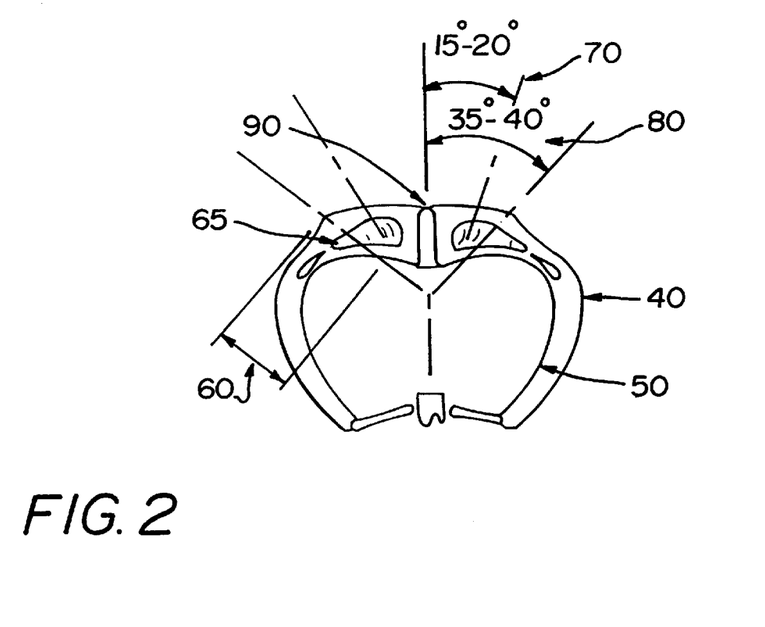
FIG. 2 is a cross sectional view taken along section line II—II of FIG. 1.

FIG. 2 is a cross sectional view taken along section line II—II of FIG. 1. The chine button 90 is located at the top of the exposed rib 50. The grain of meat generally runs at an angle 70, which is between about 15° and about 20°. It has been determined that a transducer provides an accurate signal when offset from the grain by about 20°. Thus, the transducer should be placed on the hide 40 at an angle 80 of about 35° to about 40°. Vegetable oil should be spread on the hide allowing the transducer to make better contact with the animal.

Also shown in FIG. 2 is a rib-eye steak area 65 with a given width 60 along the line perpendicular to the angle 80 at which a transducer should be positioned.

Figure 3:
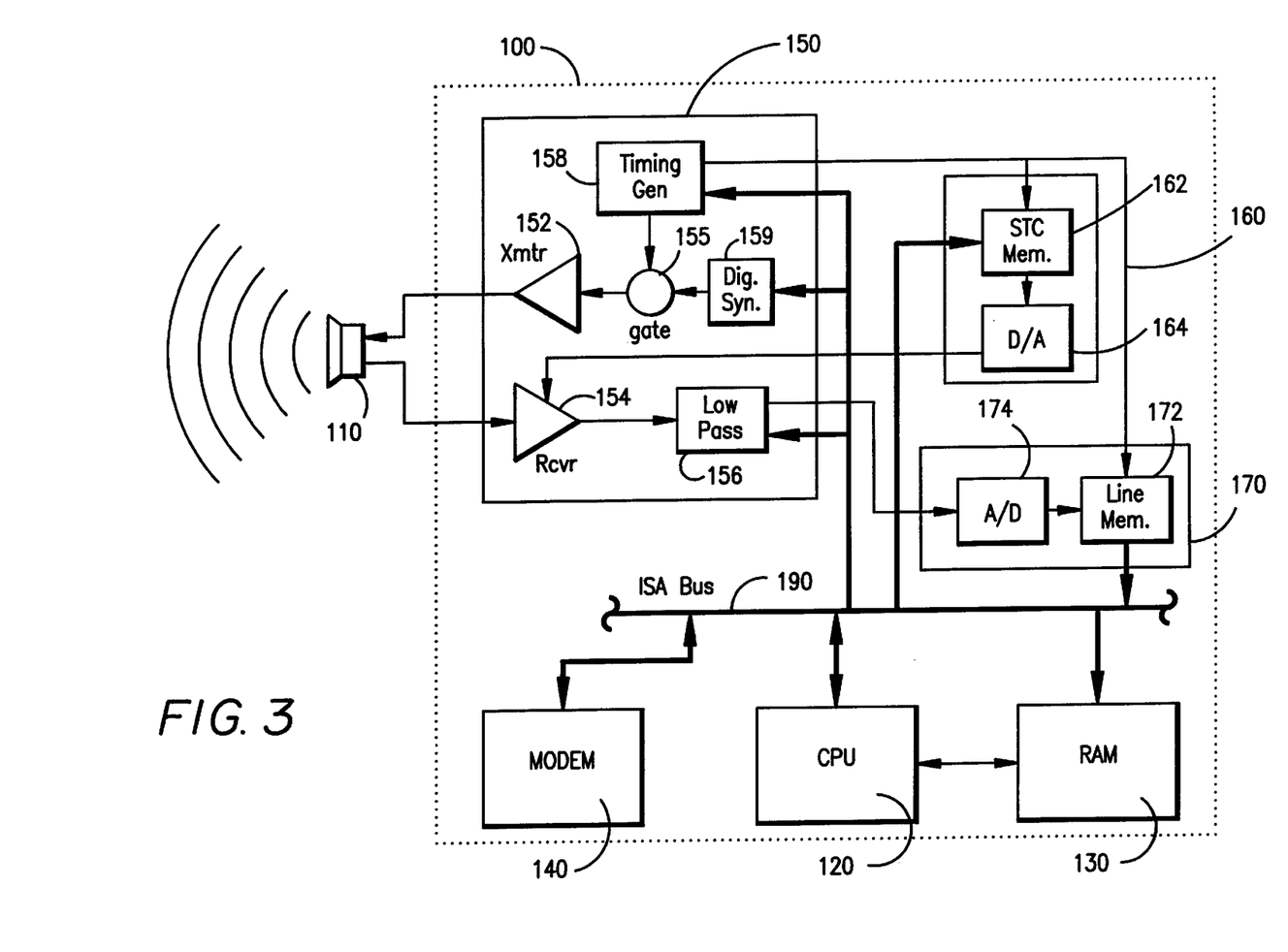
FIG. 3 shows a measuring apparatus according to a preferred embodiment of the present invention.

FIG. 3 shows a measuring apparatus according to a preferred embodiment of the present invention. A transducer probe 110 is connected to an IBM compatible computer 100 with a coaxial cable. The computer contains a CPU 120, such as a 486DX processor, connected to system random access memory (RAM) 130 through a local computer bus. Both the CPU 120 and system RAM 130 are also connected to the computer's 16 data bit industry standard architecture (ISA) bus 190. A modem 140 can also be connected to the ISA bus 190. The modem 140 can be used to transmit data through a communication network to another computer (not shown) that will analyze the data.

The transducer probe 110 is a protected face longitudinal transducer and can have a frequency of 2.25 MHz and a nominal element size of 13 mm. Such a transducer probe is the Panameterics V606-RB. A 38 mm delay line can be used with this probe to improve near surface resolution.

The transducer probe 110 communicates with the computer 100 via an ultrasonic transceiver 150. The ultrasonic transceiver 150 has a digital synthesizer 159 connected to the ISA bus 190. The digital synthesizer 159 generates a wave form which passes through gate 155 to the transmitter amplifier 152. A timing generator 158 connected to the ISA bus 190 controls the gate 155. The amplified signal is sent to the transducer probe 110 and transmitted as an ultrasonic A Scan signal into a section of tissue (not shown). The Matec Instruments TB-1000 gated amplifier Toneburst plug-in card can be used for the ultrasonic transceiver 150.

The returning ultrasonic A Scan signal is received by the transducer probe 110 and input to a receiver amplifier 154. The amplified received signal is then sent to low pass filter 156, which is connected through an analog to digital converter 174 and line memory 172, as discussed below, to ISA bus 190.

The computer 110 also has a system board 160 with a sensitivity time control (STC) memory 162, such as an Intel 27128 EPROM, controlled by the timing generator 158. The STC memory 162 is connected to the ISA bus 190 and has an 8 bit connection to the digital-to-analog converter 164, such as a DAC 0800. Sensitivity gain control curves are stored in STC memory 162 and allow the digital-to-analog converter 164 to control the gain of the receiver amplifier 154.

Finally, the computer has a digital scope 170 with an analog-to-digital converter 174. The analog-to-digital converter has an 8 bit connection to a line memory 172. The line memory is controlled by the timing generator 158 and is connected to the ISA bus 190. The analog-to-digital converter 174 receives the signal output by the low pass filter 156 in the ultrasonic transceiver 150, digitizes it and stores the results in the line memory 172.

The computer 100 can also have standard components, such as a keyboard, mouse, display terminal, operating system and printer, none of which is shown in FIG. 3.

Figure 4:
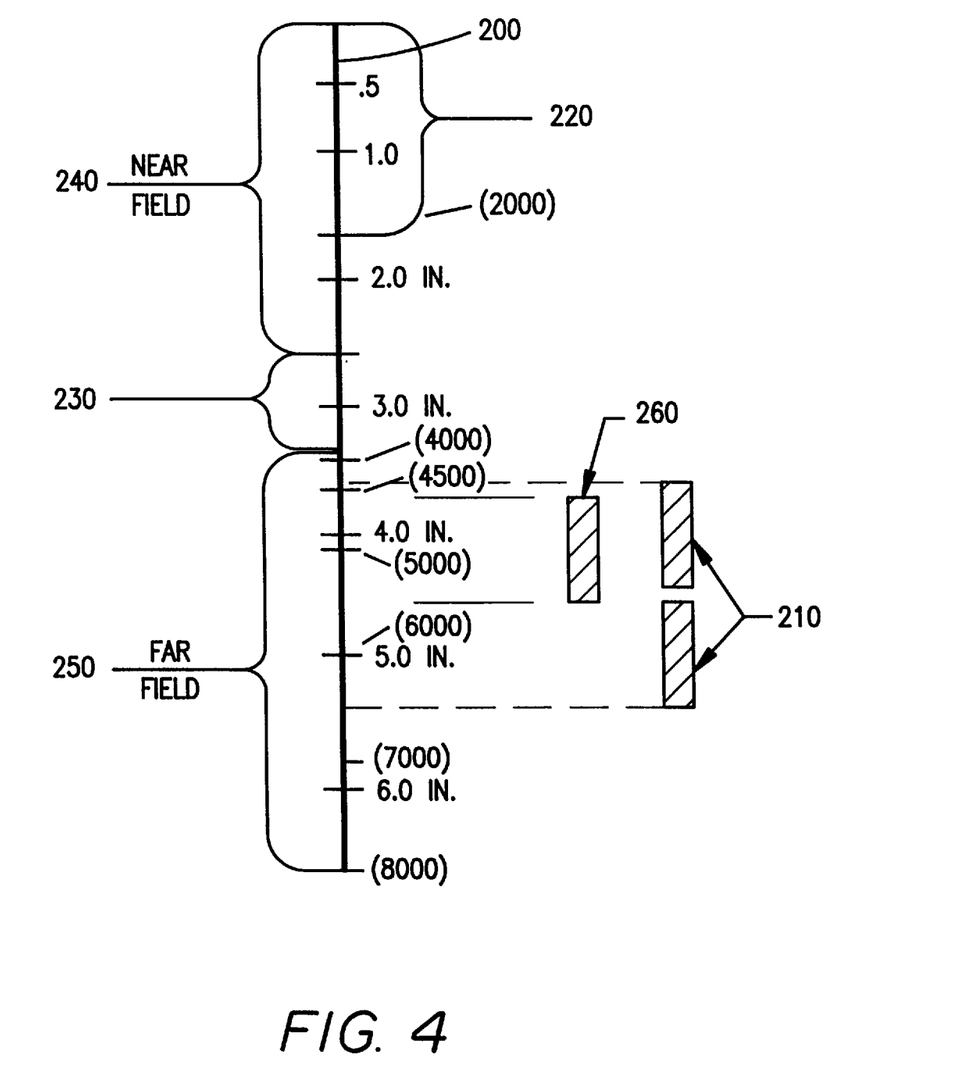
FIG. 4 shows the areas of transducer signal return according to depth.

FIG. 4 shows the areas of ultrasonic A scan signal received by transducer 110 according to penetration depth 200. Depth is shown both in terms of distance, labeled in inches, and the number of samples, shown in parenthesis. A 70 dB receiver can be expected to produce returns of approximately 8000 sample, or data, points. Using a 40 MHz sampling rate and assuming the speed of sound in tissue to be about 1540 m/sec, the entire 8000 data samples represents approximately 16 cm.

The sound field of the ultrasonic transducer contains two separate zones: the near field 240 and the far field 250. The near field 240 is the region directly in front of the transducer where the echo amplitude goes through a series of maxima and minima. The near field 240 (shown at the top of FIG. 4) can contain saturated return signals and is not used to determine the grade or merit of the meat. However, these saturated return signals can be used to determine the depth of back fat. This depth can be up to 1.5 inches. The back fat area 220 of the return signal contains 2000 data points.

The far field 250 is the area beyond the near field 240 past the point 230 where the signal decays to zero pressure. The far field 250 is the area where the best signal returns are achieved. In the present invention, the far field corresponds to the area from about three to about six inches below the hide. This is the area of interest when determining the quality of the meat. Therefore, the grade sample gate 260, used for grade and merit determinations, is located in the far field 250. The grade sample gate 260 contains 1000 data points. The two attenuation sample gates 210, used for attenuation determination, are also located in the far field 250. Each attenuation sample gate 210 contains 1000 data points.

Figure 5:
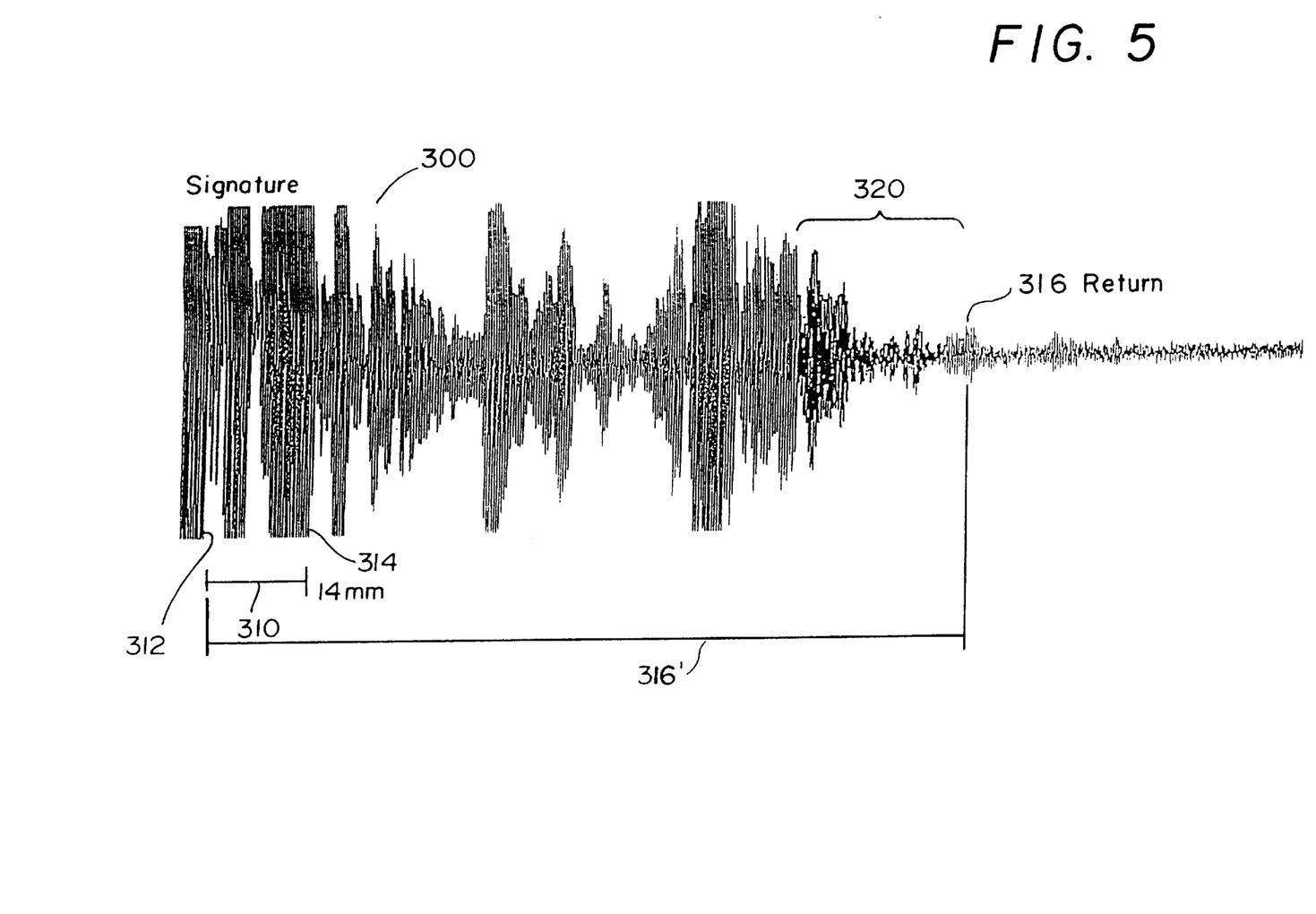
FIG. 5 shows a sample A scan transducer signature obtained with the preferred embodiment of the present invention.
Figure 11:
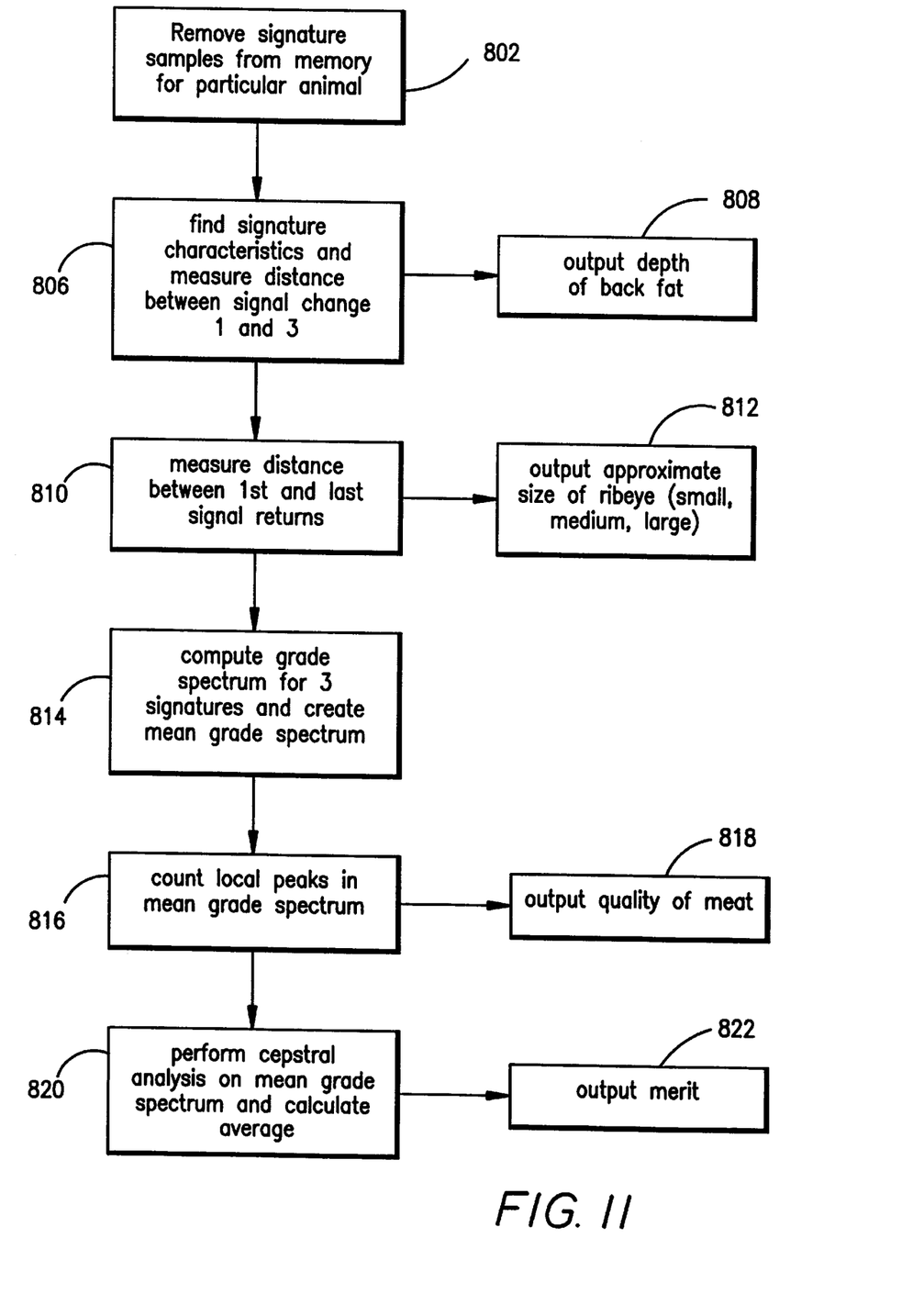
FIG. 11 shows a flow diagram of the steps performed in a preferred embodiment of the present invention.

The first step in the quantitative analysis is to convert the ultrasonic return signal data into a digital signature. FIG. 5 shows a sample A scan transducer signature 300 obtained with the preferred embodiment of the present invention. Based on the signature 300 in the near field, the depth of back fat 310 can be determined. First, three signatures are obtained by placing the transducer in the locations described with respect to FIG. 1: above the twelfth rib; above the thirteenth rib; and between the twelfth and thirteenth ribs. Each signature in the near field is examined to determine the points at which the signature decays from a high return to a small return. These signals represent changes in tissue type at that depth. The distance 310 between the first such reduction 312 and the third reduction 314 is the approximate depth of the back fat. This process is shown in FIG. 11 as steps 802, 806 and 808.

The signature 300 can also be used to measure the size of a predetermined area in the tissue, such as the rib-eye area. This can be done, for example, by measuring the distance between the first signal reduction 312 and the last signal 316 present in the signature. This distance is approximately proportional to rib eye area. This process is shown in FIG. 11 as steps 810 and 812.

Also shown in FIG. 5 is the grade sample gate area 320 of the signature 300. The grade sample gate area 320 is used for grade and merit determinations as described with respect to FIGS. 8 through 10.

Figures 6, 7:
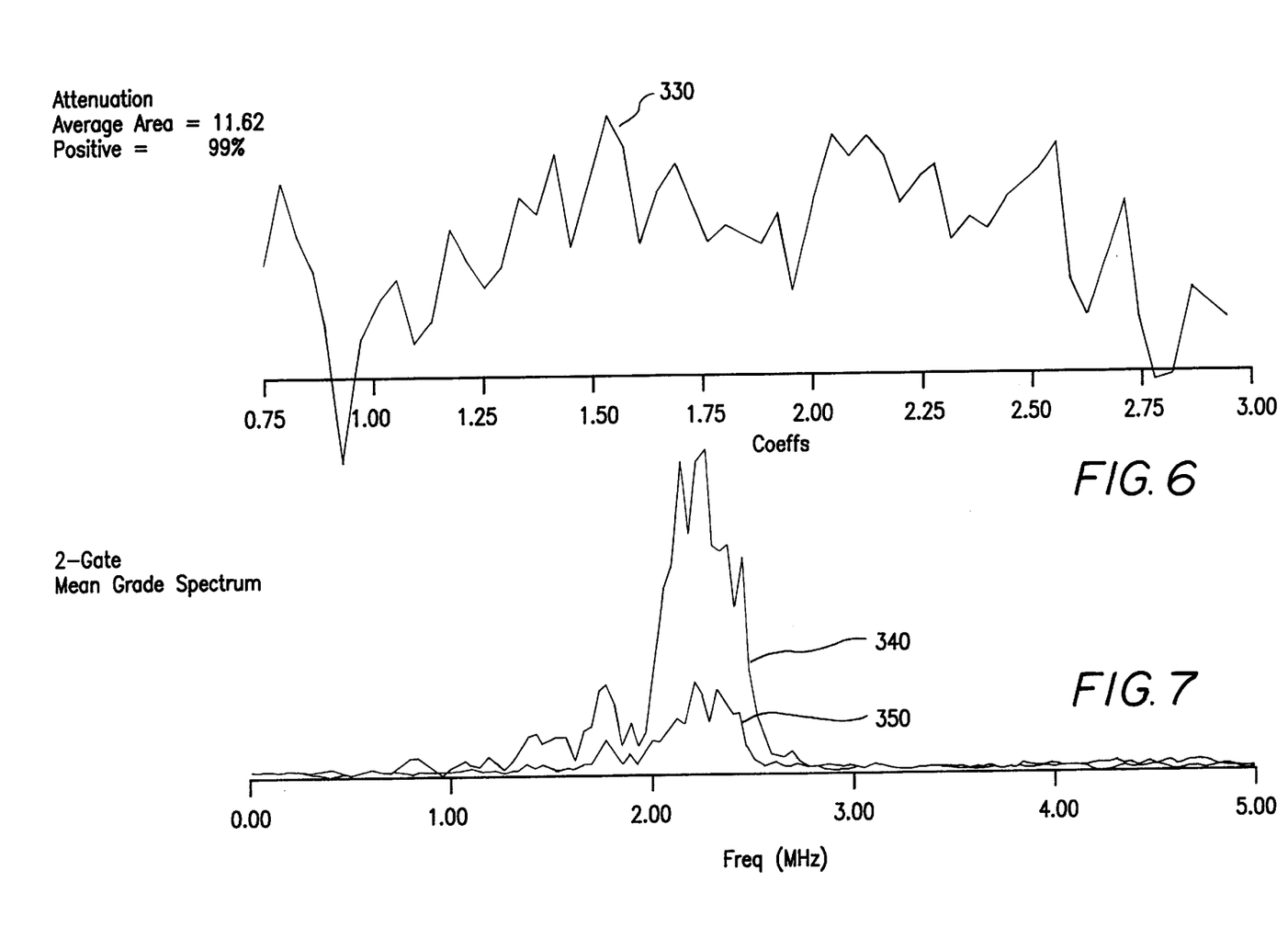
FIG. 6 shows the attenuation chart of the signature shown in FIG. 5.
FIG. 7 shows the dual gate mean grade power spectrum chart of the signature shown in FIG. 5.

FIG. 6 shows the attenuation 330 of the signature shown in FIG. 5. The attenuation 330 and 2-gate mean grade power spectrum charts 340, 350 are generated by the computer based on the data from the two attenuation sample gates 210 shown in FIG. 4. These charts provide an indication of the quality of the return signal. The attenuation chart shows the amount of signal return loss between the first and second attenuation sample gates. The attenuation 330 shown in FIG. 6 is 99% positive, which represents a very reliable return signal. It has been found that the attenuation occurring parallel to the grain of a meat sample is approximately one-half as large as the attenuation occurring perpendicular to the grain of the meat sample. Thus, if the transducer is placed on the animal at an incorrect angle, the attenuation 330 might be only 50% positive. This would indicate that the return signal was not very reliable. Similarly, a low attenuation score might indicate that the contact between the transducer and hide was poor, and more vegetable oil should have been applied.

The mean grade power spectrum charts 340, 350 shown in FIG. 7 are also calculated using the two attenuation sample gates and should display similar maxima and minima to indicate a reliable return signal. The mean grade power spectrums are calculated in a manner similar to that described with respect to FIG. 8.

Figure 8:
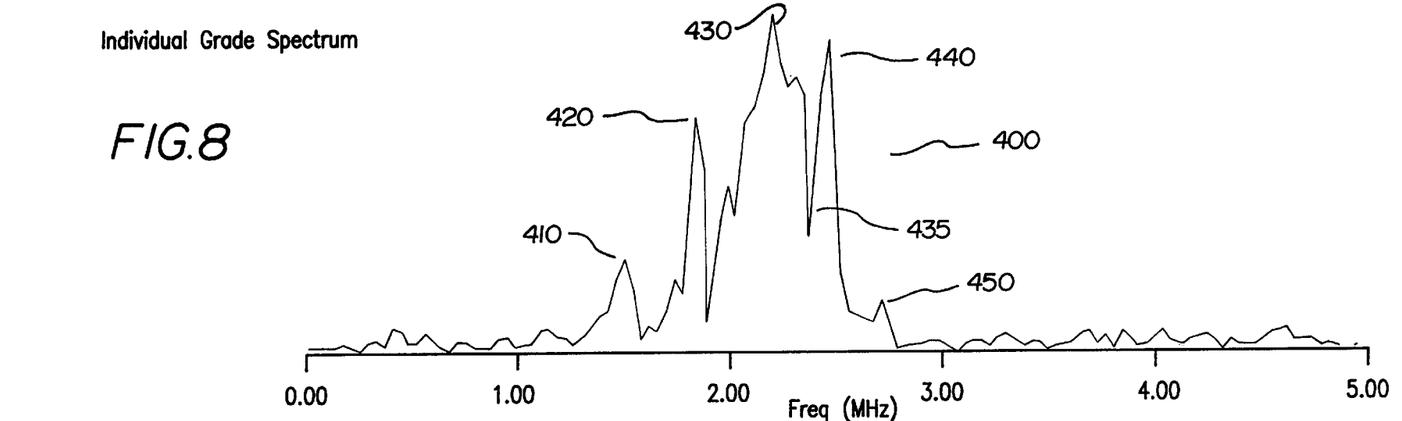
FIG. 8 shows an individual grade power spectrum of the signature shown in FIG. 5.

FIG. 8 shows the individual grade power spectrum 400 of the signature shown in FIG. 5 using the grade sample gate area 320. Generating the individual grade power spectrum is performed by converting the digitized return signal into the frequency domain by means of a fast fourier transform (FFT). FFT is a mathematical algorithm used to calculate the frequency domain, or fourier transform of a time domain signal. The FFT equation is as follows:

$$X(m) = \sum_{n0}^{N-1} x_H(n) W^{mn}$$

In other words, the FFT transforms a time domain signal into the frequency domain. The power, or grade, spectrum 400 is a quantitative measure of this signal return.

It should be noted that the "score" traditionally assigned to meat samples is roughly equivalent to the percentage of intramuscular fat the meat contains. The USDA scores, and the related USDA quality grades, are given in Table 1.

TABLE 1

Meat scores and USDA quality grades.

| Score (% fat) | USDA Quality Grade (Marbling) |
|---|---|
| 2.00–2.99 | Standard (Traces) |
| 3.00–3.99 | Select (Slight) |
| 4.00–4.99 | Low Choice (Small) |
| 5.00–5.99 | Average Choice (Modest) |
| 6.00–6.99 | High Choice (Moderate) |
| 7.00–7.99 | Low Prime (Slightly Abundant) |
| 8.00–8.99 | High Prime (Moderately Abundant) |

With respect to the individual grade power spectrum 400, several factors can cause sound to reflect in soft tissue. The first is connective tissue which is different from muscle. It is a leaner material with a different protein. The second is fat, partly because of the connective tissue that it contains. When sound passes through a junction the change of speed, or impedance, will generate an ultrasonic return. This is because of measured reflection of the medium. A muscle with no fat and no connective tissue will generate a smooth return and generate few peaks because the muscle is uniform in makeup.

Thus, the presence of maxima and minima in a grade power spectrum are related to the amount of fat, or marbling, contained in the meat. It has been determined that the number of local peaks in the FFT spectrum of a ultrasonic A Scan return signal signature generally corresponds to the percent of intramuscular fat in a sample of meat. That is, if the number of peaks in the FFT spectrum is 7, the meat contains approximately 7% fat and should be given the USDA classification of low prime.

Using the FFT, or grade, spectrum 400 of FIG. 8 as an example, it can be seen that there are five local maxima corresponding to five peaks 410, 420, 430, 440, 450. This suggests that a score of 5.00, and a USDA grade of average choice, is appropriate for the meat sample. To further refine the analysis, the number of lesser maxima can be taken into consideration as described below. Thus, the grade power spectrum of FIG. 8 has a lesser minima 435 and the score could be adjusted upward, perhaps to 5.50.

Figure 9:
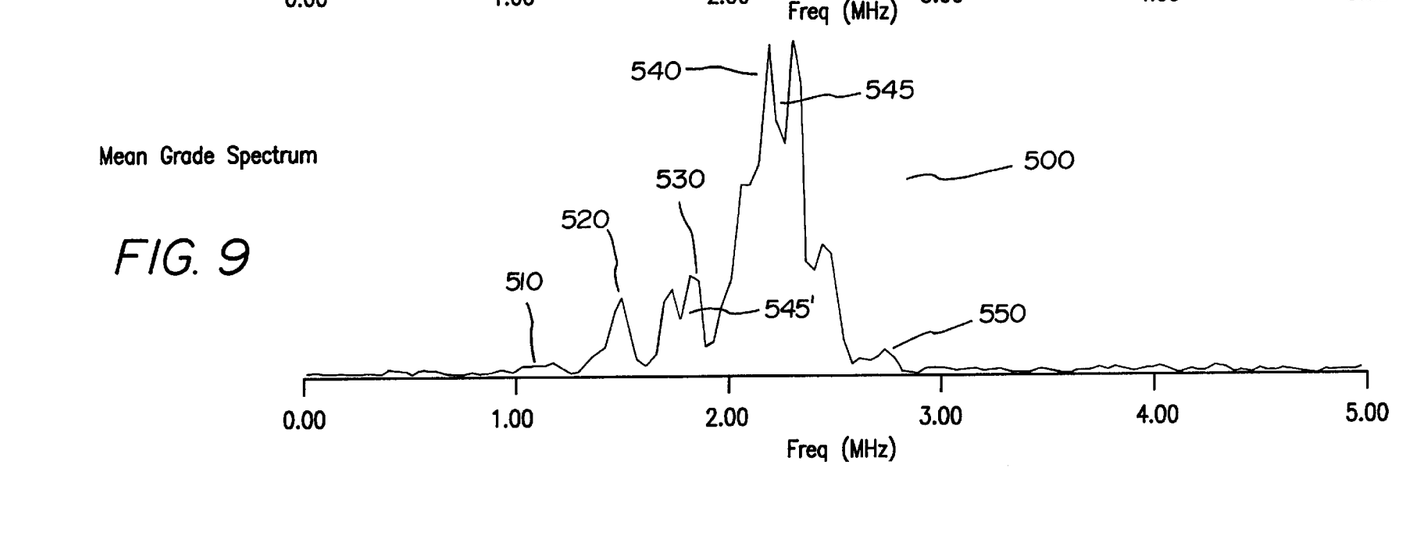
FIG. 9 shows a mean grade power spectrum for three signature samples.

FIG. 8 represents only one of the three sample signatures. To achieve a more accurate result, the grade spectrums of all three signatures should be combined. FIG. 9 shows such a mean grade power spectrum 500. The mean grade power spectrum 500 is generated using three signatures obtained by placing the transducer as described with respect to FIG. 1: above the twelfth rib; above the thirteenth rib; and between the twelfth and the thirteenth ribs. An individual grade power spectrum is generated for the grade sample gate area of each of the three signatures. The three individual grade power spectrums are combined to obtain the mean grade power spectrum 500. The mean grade power spectrum 500 can then be analyzed as described with respect to FIG. 8 to obtain a more accurate percentage of intermuscular fat and USDA grade for the meat. The five local maxima corresponding to the five peaks 510, 520, 530. 540, 550 and the minor minimas 545, 545' could represent a score of 5.50, and a USDA grade of average choice, for the meat represented by the spectrum shown in FIG. 9. This process is shown in FIG. 11 as steps 814, 816 and 818.

Figure 10:
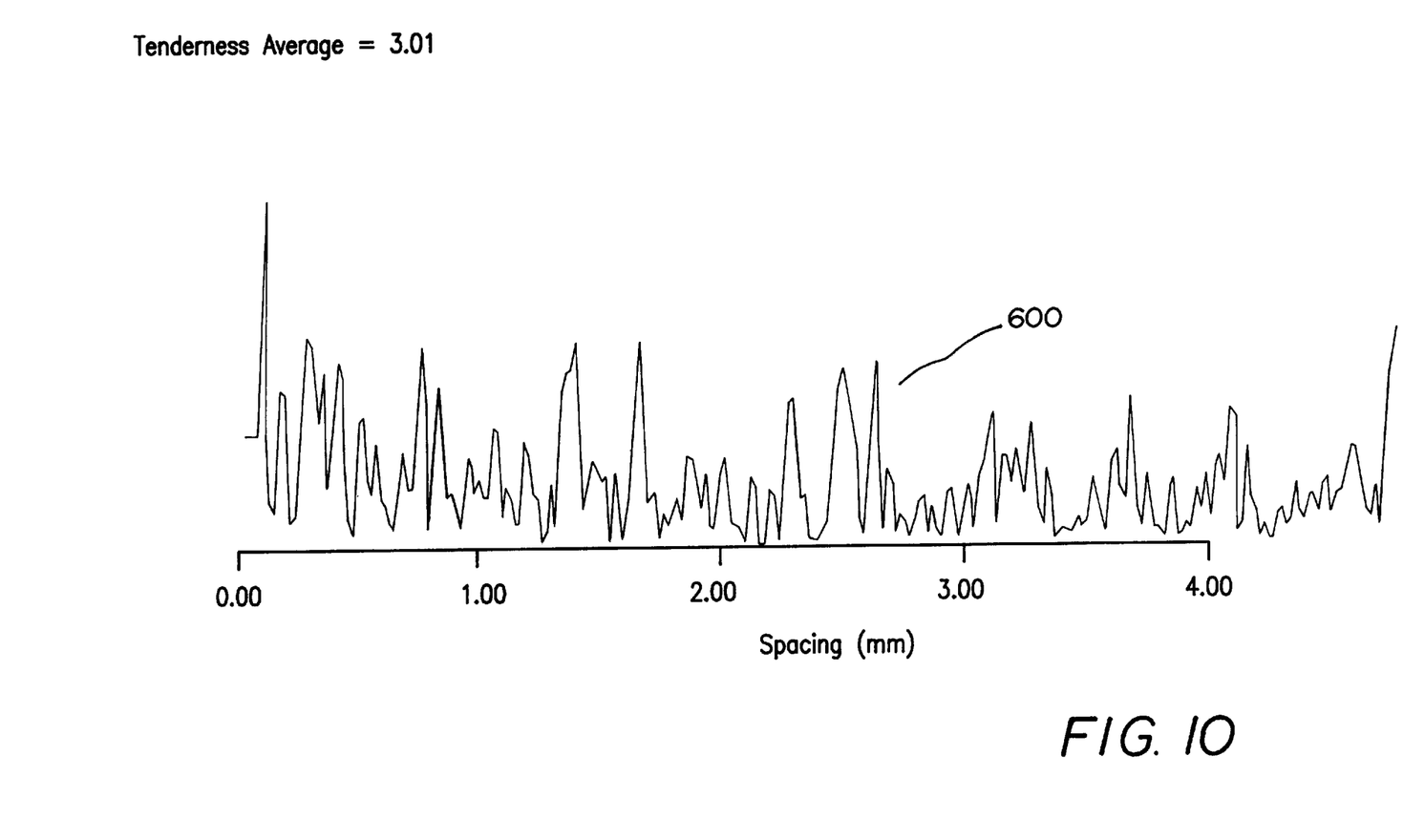
FIG. 10 shows a "merit" or tenderness chart of the mean grade power spectrum shown in FIG. 9.

FIG. 10 shows a merit number, or tenderness, chart of the mean grade power spectrum 500 shown in FIG. 9. The total energy loss of ultrasound as it moves through tissue is due to absorption, reflection and scattering. In addition to the fact that pure fat itself absorbs ultrasound, fat droplets in tissue cause scattering. This elevated attenuation of ultrasound in fatty tissue is due to increased absorption and scattering of the ultrasound energy. This suggests that fat infiltration of tissue can be evaluated quantitatively and non-invasively. It has been determined that the granular structure of the tissue corresponds to the flavor and tenderness of the meat.

The merit number is computed by performing a cepstral analysis to obtain a wave form 600. The cepstrum is obtained by performing an FFT of the log-power spectrum. The spacing between peaks in the cepstrum is called spacing among scatters (SAS). While the first FFT performed on the return signature transformed a time domain signal into the frequency domain, the cepstral analysis transforms the frequency domain signal into the distance domain. It has been determined that the average of this wave form generally corresponds to the merit of the tissue sample. That is to say, given two pieces of meat with the same USDA grade, the meat with the lower average will generally be of a higher quality in terms of tenderness and flavor. This process is shown in FIG. 11 as steps 820 and 822.

Figure 12:
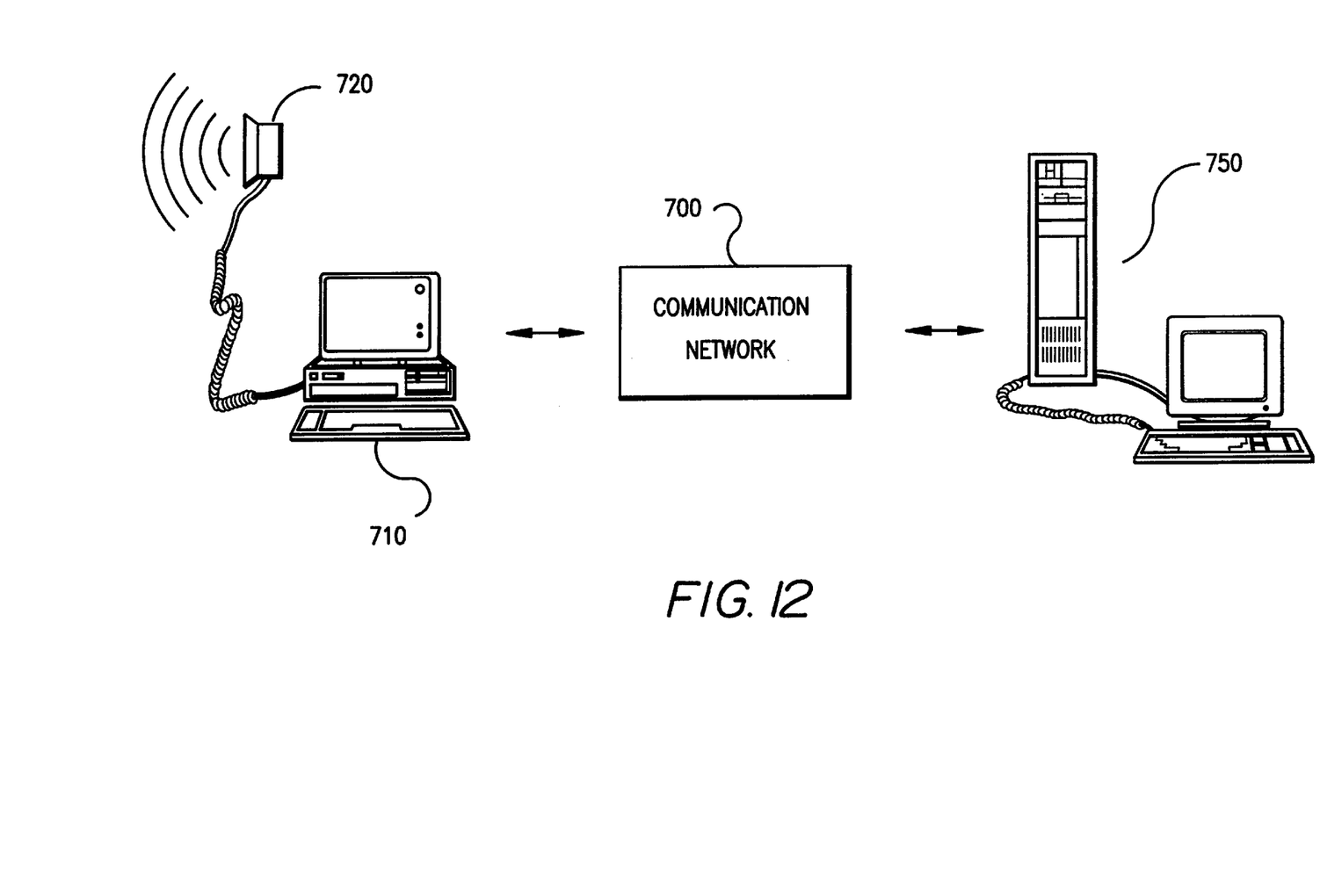
FIG. 12 shows the components of a measuring system according to a preferred embodiment of the present invention.

FIG. 12 shows the components of a measuring system according to a preferred embodiment of the present invention. A transducer 720 is connected to a first computer station 710 to record and digitize three signatures as described above for each sample of tissue. This data is transmitted through a communication network 700, such as the public telephone lines, the Internet or an Intranet to a second computer station 750. For example, the first computer station 710 could exchange data with the second computer station 750 via e-mail. The second computer station 750 analyzes the signatures as described with respect to FIGS. 6 through 10 to measure characteristics of the tissue. In the preferred embodiment of the present invention, the second computer station 750 is the server and the first computer station 710 is the client. Both computer stations 710, 750 can use the Microsoft Windows NT operating system version 4.0 or higher to handle telephone, Internet or Intranet communications. Using this configuration, many client computers 710 can be connected to a single server computer 750. The server computer 750 can verify the identity of a client computer 710 before processing the information. Moreover, the software used to analyze the ultrasonic return signatures only needs to be updated on the second computer 750 for improvements to the entire system.

Figure 13:
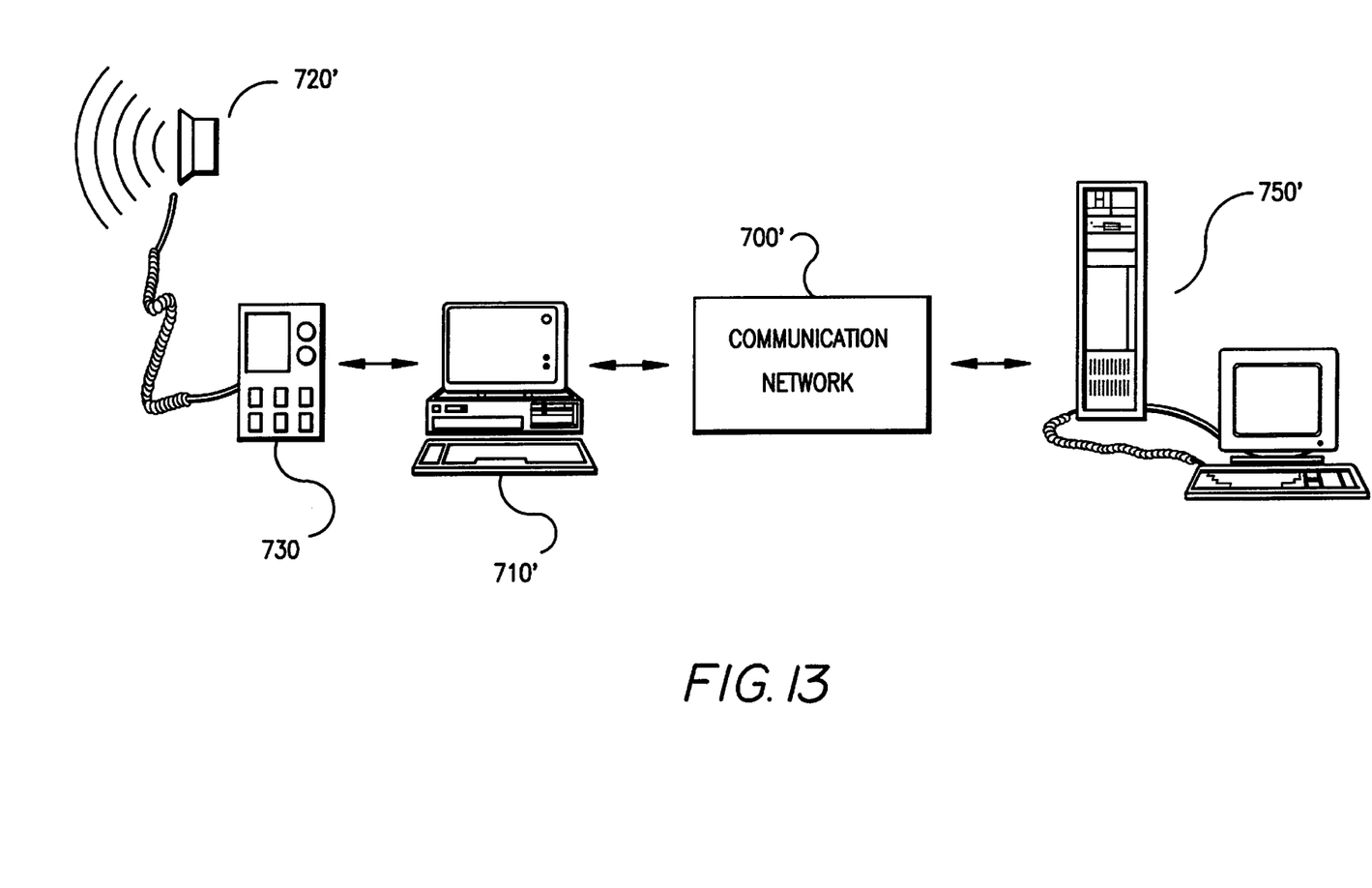
FIG. 13 shows the components of a measuring system according to another preferred embodiment of the present invention.

FIG. 13 shows the components of a measuring system according to another preferred embodiment of the present invention. A transducer 720' is connected to a hand held general purpose ultrasonic detector/collector 730, similar to the Panametrics Epoch IIIB. The hand-held detector/collector stores the digital signatures, which can be transferred to a first computer station 710' at a later time. As in the previous embodiment, this data is transmitted through a communication network 700' to a second computer station 750'. The second computer station 750' analyzes the signatures as described with respect to FIGS. 6 through 10 to measure characteristics of the tissue.

With either of the above embodiments, the second computer station 750, 750' can report the results of the measurements back to the first computer station 710, 710' through the communication network 700, 700' either on a sample-by-sample basic or in the form of a report containing a plurality of samples. Either the first computer station 710, 710' or the second computer station 750, 750' can use this information to create and maintain a database regarding a particular animal or a group of animals. The reports and database can be arranged based on the age of the animals, the quality of the meat, the date the signatures were taken, the genetic or family history of an animal, the owner of the animal, or any other identifying feature. These reports can then be used by the animal owners or feedlots to improve the quality of the herd.

Figure 14:
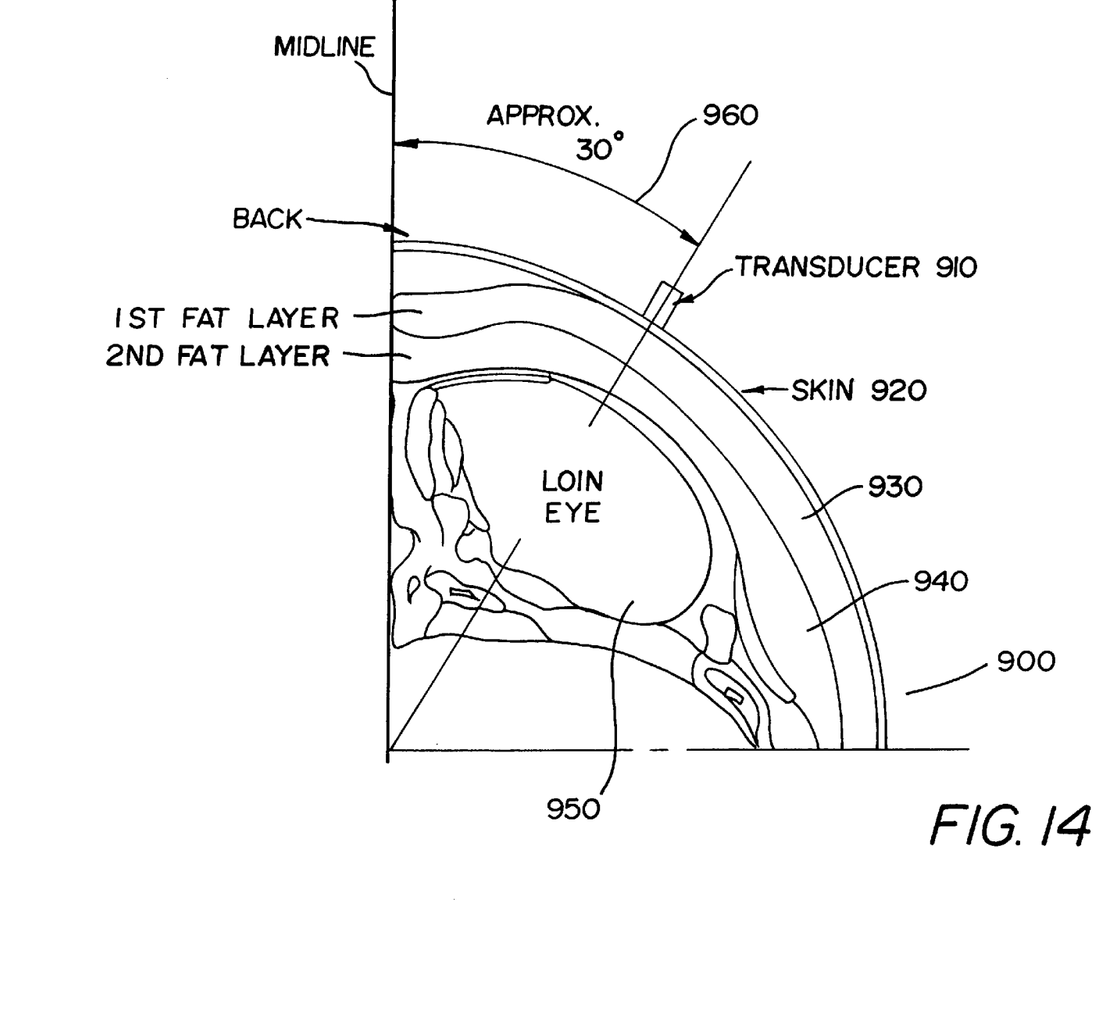
FIG. 14 shows a cross sectional skeletal view of a hog taken at the tenth rib.

While the above embodiments are directed to determining the characteristics of tissue on a beef animal, a similar approach could be used with hogs. FIG. 14 shows a cross sectional skeletal view of a hog 900 taken at the tenth rib. A transducer 910 can be placed on the hog's skin 920 at a predetermined angle 960. A process similar to that described with respect to FIGS. 3 through 11 can then be used to perform a quantitative analysis of ultrasonic A scan signals.

The sensitivity gain control curves stored in STC memory 162 may need to be customized to handle the ultrasonic return signals associated with hogs. Because the STC memory 162 can store multiple sensitivity gain control curves, it is possible that a single machine could store separate curves for beef animals and hogs. The operator could then chose the appropriate curve depending on the type of meat being examined.

Pork is assigned a quality grade in a manner similar to the grading of beef. Thus, a similar process can be used to determine the percentage of internal fat, the quality grade, and the merit number of the pork tissue. Moreover, as shown in FIG. 13, hogs have two layers of back fat 930, 940. The ultrasonic return signal can be analyzed to determine the depth of these back fat layers and the approximate size of a predetermined loin eye area 950. The ultrasonic A scan should be measured at the tenth rib, the last rib and in between the tenth and last rib.

Although preferred embodiments are specifically illustrated and described herein, it will be appreciated that modifications and variations of the present invention are covered by the above teachings and within the purview of the appended claims without departing from the spirit and intended scope of the invention.

What is claimed as new and desired to be secured by Letters Patent of the United States is:

1. A method of measuring characteristics of meat, comprising the steps of:
   transmitting an ultrasonic signal into the meat using an A scan ultrasonic transducer;
   receiving a return of said ultrasonic signal using said A scan transducer; and
   determining a characteristic of the meat by performing a fast fourier transform on said return signal.

2. A method of measuring characteristics of meat according to claim 1, wherein said steps of transmitting and receiving are performed a plurality of times to generate a plurality of return signals and said step of determining is performed using said plurality of return signals.

3. A method of measuring characteristics of meat according to claim 2, wherein said plurality of return signals are combined.

4. A method of measuring characteristics of meat according to claim 3, wherein said plurality of return signals are averaged.

5. A method of measuring characteristics of meat according to claim 1, wherein the meat is beef and said steps of transmitting and receiving are performed over the twelfth rib, thirteenth rib and between the twelfth and the thirteenth rib of the beef animal.

6. A method of measuring characteristics of meat according to claim 5, wherein the characteristic of the meat is the thickness of back fat on the beef animal.

7. A method of measuring characteristics of meat according to claim 6, wherein said step of determining comprises a step of measuring a frequency difference between a first reduction in the return signal and a third reduction in the return signal.

8. A method of measuring characteristics of meat according to claim 1, wherein the meat is on an animal that is alive.

9. A method of measuring characteristics of meat according to claim 1, wherein the meat is on an animal that has been processed.

10. A method of measuring characteristics of meat according to claim 1, wherein the meat is on a hog.

11. A method of measuring characteristics of meat according to claim 1, wherein the characteristic of the meat is the percentage of intramuscular fat contained in the meat.

12. A method of measuring characteristics of meat according to claim 1 wherein said steps of transmitting and receiving are performed a plurality of times to generate a plurality of return signals and said step of determining is performed using said plurality of return signals.

13. A method of measuring characteristics of meat according to claim 1, wherein the characteristic of the meat is the USDA quality grade of the meat.

14. A method of measuring characteristics of meat according to claim 13, wherein said step of determining comprises the steps of:
   performing a fast fourier transform on said return signal to generate a power spectrum,
   counting the number of local peaks in said power spectrum, and
   determining the USDA quality grade of the meat based on said number of local peaks.

15. A method of measuring characteristics of meat according to claim 14, wherein said steps of transmitting and receiving are performed a plurality of times to generate a plurality of return signals and said step of determining is performed using said plurality of return signals.

16. A method of measuring characteristics of meat according to claim 1, wherein the characteristic of the meat is a merit number representing the flavor and tenderness of the meat.

17. A method of measuring characteristics of meat according to claim 16, wherein said step of determining comprises the steps of:
   performing a first fast fourier transform on said return signal to generate a power spectrum,
   performing a second fast fourier transform on a log power of said power spectrum to generate a cepstrum, and
   determining the merit number of the meat based on said cepstrum.

18. A method of measuring characteristics of meat according to claim 17, wherein said steps of transmitting and receiving are performed a plurality of times to generate a plurality of return signals and said step of determining is performed using said plurality of return signals.

19. A method of measuring characteristics of meat according to claim 1, wherein the characteristic of the meat is the approximate size of a predetermined area in the meat.

20. A method of measuring characteristics of meat according to claim 19, wherein said step of determining comprises a step of measuring a frequency difference between a first reduction in the return signal and a last return signal.

21. A method of measuring characteristics of meat according to claim 1, wherein said transducer is a longitudinal transducer.

22. A method of measuring characteristics of meat according to claim 1, wherein said transducer has a frequency of approximately 2.25 MHz.

23. The method of measuring characteristics of meat according to claim 1, wherein said fast fourier transform is performed on said return signal to obtain a power spectrum, and where the number of local peaks in the power spectrum are counted to determine the percentage of intramuscular fat contained in the meat.

24. An apparatus for measuring characteristics of meat, comprising:
   an A scan transducer that transmits an ultrasonic signal into the meat and receives a return signal; and
   a computer connected to receive said return signal from said A scan transducer, said computer converting said return signal to the frequency spectrum by a fast fourier transform and determining a characteristic of the meat based on characteristics of said fourier transformed return signal.

25. An apparatus for measuring characteristics of meat according to claim 24, wherein said computer receives said return signal through the public telephone network.

26. An apparatus for measuring characteristics of meat according to claim 24, wherein said computer receives said return signal through the Internet.

27. An apparatus for measuring characteristics of meat according to claim 24, wherein the characteristic of the meat is the USDA quality grade of the meat.

28. An apparatus for measuring characteristics of meat according to claim 27, wherein said computer determines the USDA quality grade of the meat based on the local peaks in a power spectrum obtained by a fast fourier transform on said return signal.

29. An apparatus for measuring characteristics of meat according to claim 24, wherein the characteristic of the meat is a merit number representing the flavor and tenderness of the meat.

30. An apparatus for measuring characteristics of meat according to claim 29, wherein said computer determines the merit number of the meat based on a cepstral analysis of said return signal.

31. An apparatus for measuring characteristics of meat according to claim 24, wherein the characteristic of the meat is the thickness of back fat in an animal.

32. An apparatus for measuring characteristics of meat according to claim 24, wherein the characteristic of the meat is the approximate size of a predetermined area in the meat.

33. An apparatus for measuring characteristics of meat according to claim 24, wherein said transducer is a longitudinal transducer.

34. An apparatus for measuring characteristics of meat according to claim 24, wherein said transducer has a frequency of approximately 2.25 MHz.

35. An apparatus for measuring characteristics of meat according to claim 24, wherein said computer determines a percentage of intramuscular fat contained in the meat based on the number of local peaks which appear in a power spectrum obtained by performing the fast fourier transform on said return signal.

36. A method of monitoring the genetic characteristics of a plurality of beef animals, comprising:

assigning each of said plurality of beef animals an identification number;

transmitting an ultrasonic signal into each of said plurality of beef animals using an A scan ultrasonic transducer;

receiving a return signal of said ultrasonic signal for each of said plurality of beef animals using said A scan transducer;

determining the characteristics of each of said plurality of beef animals by performing a fast fourier transform on said return signal; and storing said identification numbers and their associated meat characteristics in a database.

37. A method of monitoring the genetic characteristics of a plurality of beef animals according to claim 36, wherein said database further includes information related to the genealogy of said meat animals.

38. A method of monitoring the genetic characteristics of a plurality of beef animals according to claim 36, wherein said database includes for each identification number multiple associated meat characteristics measured when the associated beef animal was at different ages.

39. A method of monitoring the genetic characteristics of a plurality of beef animals according to claim 36, further comprising the step of generating a report based on the information in said database.

40. A method of monitoring the genetic characteristics of a plurality of beef animals according to claim 39, wherein said report contains information regarding the genetic history of animals.

41. A method of monitoring the genetic characteristics of a plurality of beef animals according to claim 39, wherein said report contains information related to a subset of said plurality of beef animals.

42. A method of monitoring the genetic characteristics of a plurality of beef animals according to claim 39, wherein said report is generated automatically.

43. A method of monitoring the genetic characteristics of a plurality of beef animals according to claim 39, wherein said report is generated when requested by a user.

44. The method of monitoring the genetic characteristics of a plurality of beef animals of claim 36, wherein said fast fourier transform is used to generate a power spectrum, and where the number of local peaks in the power spectrum are counted to determine the percentage of intramuscular fat contained in each of said plurality of beef animals.

* * * * *